United States Patent
Perraud et al.

(10) Patent No.: US 11,116,970 B2
(45) Date of Patent: Sep. 14, 2021

(54) CUTANEOUS DEVICE, IN PARTICULAR A PULSE GENERATOR FOR ELECTRICAL STIMULATION

(71) Applicant: COMMISSARIAT A L'ENERGIE ATOMIQUE ET AUX ENERGIES ALTERNATIVES, Paris (FR)

(72) Inventors: Simon Perraud, Bandol (FR); Nicolas Karst, Folkling (FR); Jérémie Salomon, Villard-de-Lans (FR)

(73) Assignee: COMMISSARIAT A L'ENERGIE ATOMIQUE ET AUX ENERGIES ALTERNATIVES, Paris (FR)

(*) Notice: Subject to any disclaimer, the term of this patent is extended or adjusted under 35 U.S.C. 154(b) by 0 days.

(21) Appl. No.: 15/309,541

(22) PCT Filed: May 7, 2015

(86) PCT No.: PCT/IB2015/053340
§ 371 (c)(1),
(2) Date: Nov. 8, 2016

(87) PCT Pub. No.: WO2015/177670
PCT Pub. Date: Nov. 26, 2015

(65) Prior Publication Data
US 2017/0136228 A1 May 18, 2017

(30) Foreign Application Priority Data
May 19, 2014 (FR) .................................... 1454466

(51) Int. Cl.
*A61N 1/04* (2006.01)
*A61N 1/36* (2006.01)

(52) U.S. Cl.
CPC ....... *A61N 1/36014* (2013.01); *A61N 1/0452* (2013.01); *A61N 1/0456* (2013.01);
(Continued)

(58) Field of Classification Search
CPC ................ A61N 1/0456; A61N 1/0452; A61N 1/36014; A61N 1/36021; A61N 1/36003; A61N 1/0492
See application file for complete search history.

(56) References Cited

U.S. PATENT DOCUMENTS 4,690,144 A * 9/1987 Rise .................... A61N 1/36014
607/59
5,195,517 A * 3/1993 Chen .................. A61N 1/36014
128/907

(Continued)

OTHER PUBLICATIONS

Written Opinion of the International Searching Authority dated Jul. 30, 2015, issued in corresponding International Application No. PCT/IB2015/053340, filed May 7, 2015, 4 pages.

(Continued)

*Primary Examiner* — George R Evanisko
(74) *Attorney, Agent, or Firm* — Christensen O'Connor Johnson & Kindness PLLC

(57) ABSTRACT

A substantially planar device intended to be secured to the skin of a user is disclosed. The device includes components and electrical connection means defining at least one rigid zone of the device. The electrical connection means have, in the plane of the device, a surface corresponding to at least one component and the means are disposed such as to cover the at least one component in order to protect the component mechanically.

16 Claims, 7 Drawing Sheets

Figure 1B:
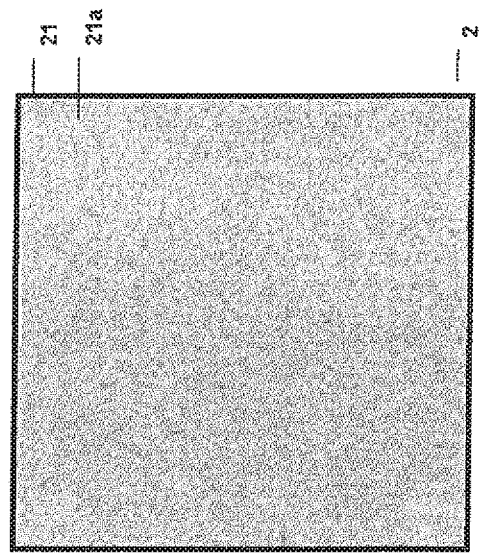

(52) U.S. Cl.
CPC ....... *A61N 1/0492* (2013.01); *A61N 1/36003* (2013.01); *A61N 1/36021* (2013.01)

(56) References Cited

U.S. PATENT DOCUMENTS

| | | | | |
|---|---|---|---|---|
| 5,387,189 | A * | 2/1995 | Gory | A61N 1/0412 604/20 |
| 5,562,607 | A * | 10/1996 | Gyory | A61N 1/0436 604/20 |
| 5,562,718 | A * | 10/1996 | Palermo | A61N 1/36021 607/46 |
| 6,355,025 | B1 * | 3/2002 | Phipps | A61N 1/30 604/20 |
| 8,086,318 | B2 * | 12/2011 | Strother | A61N 1/0456 607/2 |
| 8,332,009 | B2 * | 12/2012 | McLaughlin | A61B 5/0416 600/372 |
| 2009/0076345 | A1 * | 3/2009 | Manicka | A61B 5/04087 600/301 |
| 2012/0232634 | A1 * | 9/2012 | Fisher, III | A61N 1/048 607/149 |
| 2013/0023816 | A1 | 1/2013 | Bachinski et al. | |
| 2013/0197341 | A1 | 8/2013 | Grob et al. | |
| 2013/0226275 | A1 * | 8/2013 | Duncan | A61N 1/0492 607/152 |
| 2014/0046416 | A1 * | 2/2014 | Bennett | A61N 1/0502 607/116 |

OTHER PUBLICATIONS

International Preliminary Report on Patentability dated Nov. 22, 2016, issued in corresponding International Application No. PCT/IB2015/053340, filed May 7, 2015, 1 page.
Rapport de Recherche Préliminaire dated Sep. 5, 2014, issued in priority French Application No. 1454466, filed May 19, 2014, 1 page.
International Search Report dated Jul. 30, 2015, issued in corresponding International Application No. PCT/IB2015/053340, filed May 7, 2015, 3 pages.

* cited by examiner

CUTANEOUS DEVICE, IN PARTICULAR A PULSE GENERATOR FOR ELECTRICAL STIMULATION

The invention relates to the technical field of devices intended to be attached on the skin of a user.

These are notably medical devices, such as cutaneous electrodes for measuring physiological parameters or pulse generators for electrical stimulation.

It is recalled here that electrical stimulation is a technique consisting of electrically stimulating nerves or muscles. Electric stimulation of nerves (notably the transcutaneous electrical stimulation technique of nerves, or transcutaneous electrical nerve stimulation or TENS) gives the possibility of treating pain. Electrical stimulation of muscles (neuromuscular electrical stimulation or NMES) is used for rehabilitation or musculation purposes.

Electrical stimulation devices comprise a generator of electric pulses connected to cutaneous electrodes. The pulse generator appears as a voluminous and rigid case and gives the possibility of sending electric pulses calibrated in frequency and in intensity as far as a specific area of the human body via electrodes.

As an example, a pulse generator as described in document Mark Johnson, Transcutaneous Electrical Nerve Stimulation (Johnson, Mark I (October 2012), Transcutaneous Electrical Nerve Stimulation (TENS), eds, John Wiley & Sons, Ltd: Chichester) appears as a case with a volume of the order of several tens of cubic centimeters and a thickness of the order of a few centimeters.

This type of pulse generator is not practical for use. Indeed, this is a cumbersome object which is connected to cutaneous electrodes via relatively long electric cables.

It has been proposed in the prior art to replace the conventional, voluminous and rigid pulse generators with fine and flexible pulse generators which may be directly worn by the user as patches.

Such a fine and flexible pulse generator appearing as a patch, is described in document U.S. Pat. No. 5,423,874.

In this patch, are assembled, on a flexible circuit the energy source consisting of a battery and the electronic components which are discrete components and integrated circuits which allow operation of the pulse generator.

The flexible circuit is encapsulated between an impervious upper layer and a lower adhesive layer. The upper impervious layer plays the role of a barrier to humidity for protecting the energy source and the electronic components. The lower adhesive layer, which comprises two electrodes, gives the possibility of attaching the pulse generator on the skin.

This pulse generator is less cumbersome than the conventional pulse generators and it gives the possibility of considerably reducing the length of the electrical cables, or even to completely do without these cables.

However, a device as described in document U.S. Pat. No. 5,423,874 does not provide excellent reliability. Indeed, given that the upper and lower encapsulation layers are fine and flexible layers, the components of the device do not benefit from efficient mechanical protection, notably against impacts, piercing or stresses during the flexure of the device.

The object of the invention is to overcome these drawbacks by proposing a device intended to be attached on the skin of a user which is both fine, flexible and robust.

This device may notably form a pulse generator for electrical stimulation appearing as a patch.

This device may find other applications, notably in portable electronic devices or further in electronic devices integrated into a textile.

Thus, the invention relates to a device intended to be attached on the skin of the user, substantially planar and comprising components as well as electric connection means defining at least one rigid area of the device, the electrical connection means having, in the plane of the device, a surface corresponding to at least one component and being positioned so as to cover said at least one component for ensuring its mechanical protection.

Thus, the fact that the electrical connection means also ensure a mechanical protection function gives the possibility of ensuring the reliability and the robustness of the cutaneous device while improving its compactness and reducing its thickness.

Preferably, the electrical connection means define at least two rigid areas electrically and mechanically connected through a flexible area, said rigid areas bearing components.

The connection means advantageously have, in the plane of the device, an upper surface relatively to the one occupied by said components and are aligned with said components according to the thickness of at least one rigid area, so as to cover them.

Preferably, said electrical connection means include at least one hole intended to cooperate with a protrusion of a plug connected to an electric conductor.

Said electrical connection means advantageously also fulfill a magnetic function, so as to facilitate the connection between the electrical connection means of the device and electrical connection means of another element, for example the protrusion of a plug.

The device may comprise a stack of two layers with a first layer comprising said electrical connection means and a second layer comprising said components, mounted on a flexible circuit.

The device may then advantageously comprise a third flexible layer, in contact with said second layer, in order to ensure its encapsulation.

In a first alternative, said electrical connection means are advantageously made in a metal material and notably a ferromagnetic material.

In a second alternative, said electrical connection means comprise two parts assembled on a support in a polymeric material, one fulfilling an electrical function and the other one a magnetic function.

When two electrical connection means are located in two adjacent rigid areas and separated by a flexible area of width L, they preferably have a height H which satisfies the inequality $L<\pi H$ and preferably the inequality $L<2H$.

By this arrangement, the electrical connection means also fulfill a function for limiting the flexure of the device in the flexible areas.

The device according to the invention advantageously comprises at least one complementary rigid element positioned on the face of the device opposite to said electrical connection means and aligned, in at least one rigid area, with said components.

This complementary rigid element contributes to the mechanical protection of the components of the device.

The invention also relates to an assembly including a device according to the invention and at least one plug connected to an electric conductor, said plug including electrical connection means which may cooperate with electrical connection means of said device.

Said plug includes a part advantageously fulfilling a magnetic function.

Figure 1D:
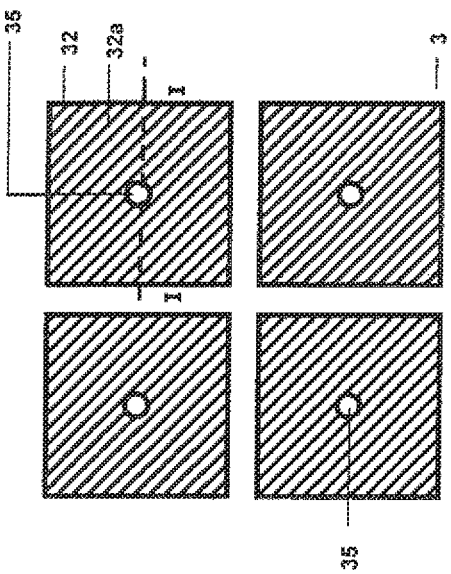
Figure 1A:
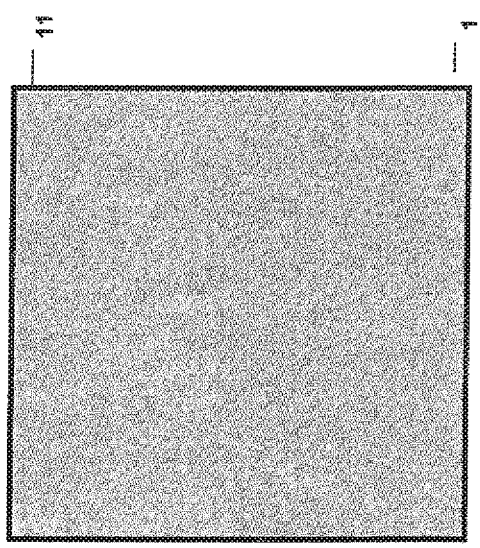
Figure 1C:
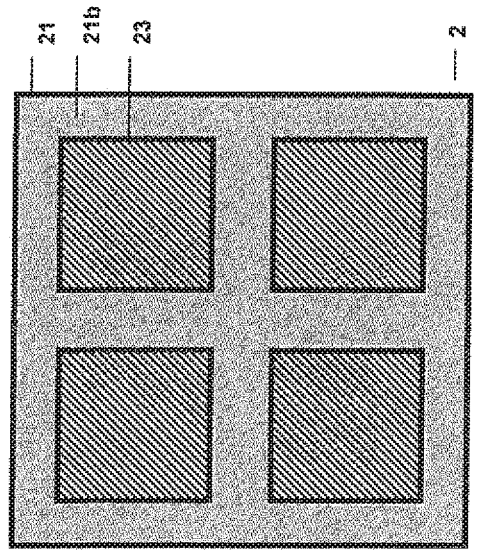
Figure 2:
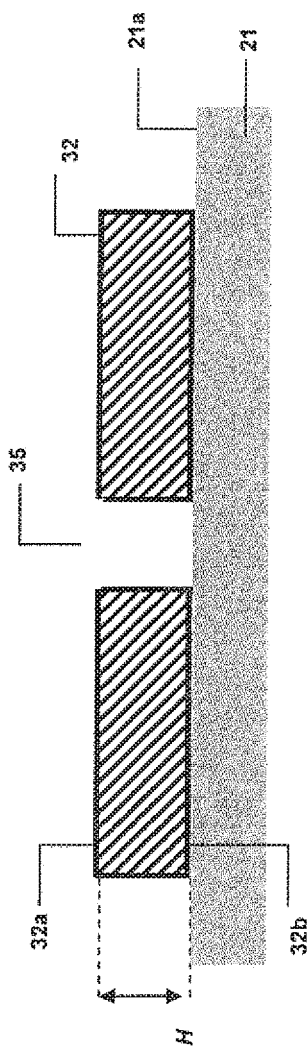
Figure 3:
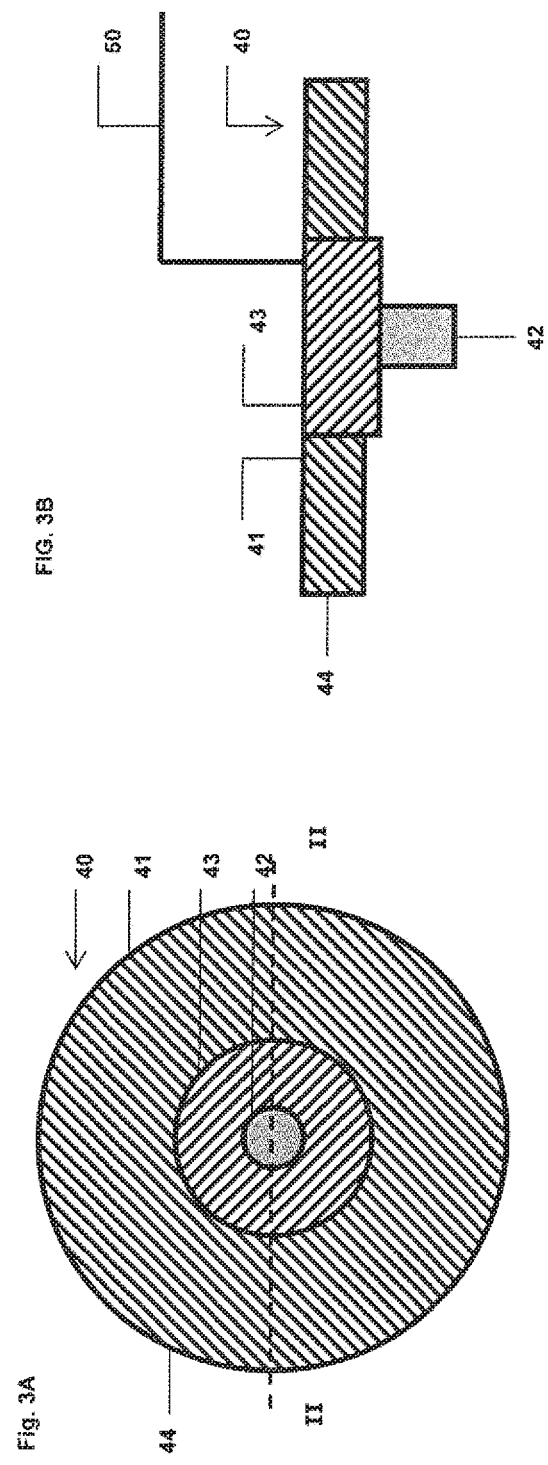
Figure 3C:
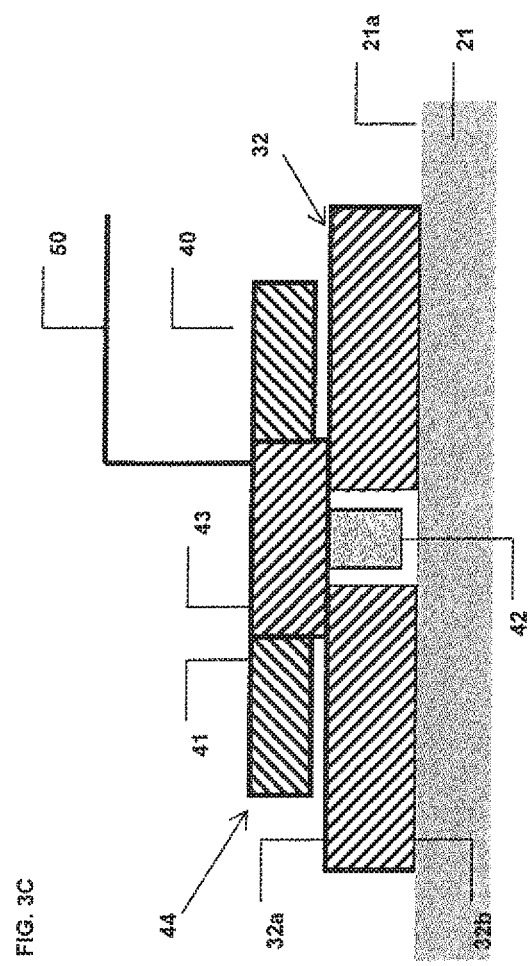
Figure 4:
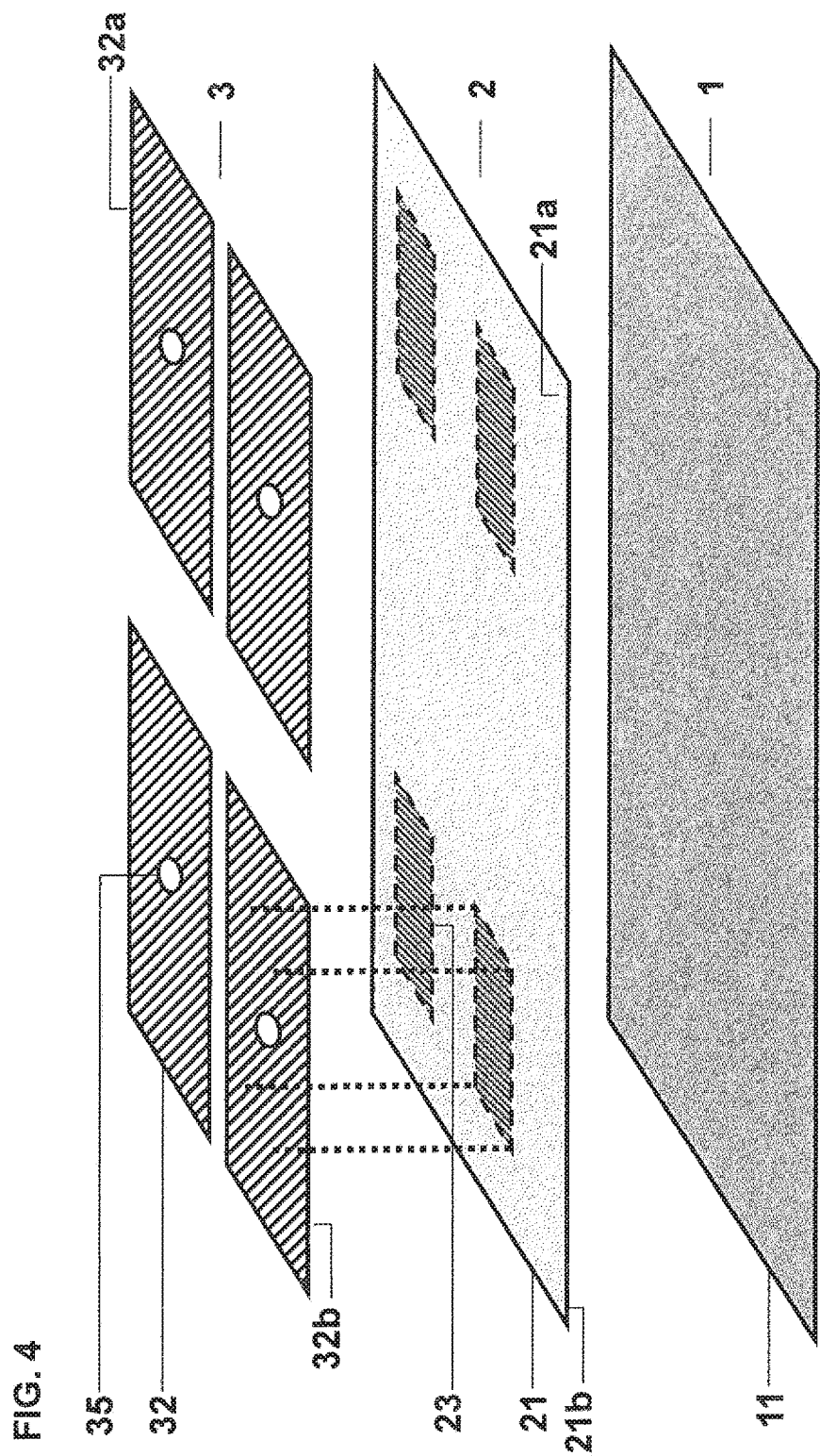
Figure 5A:
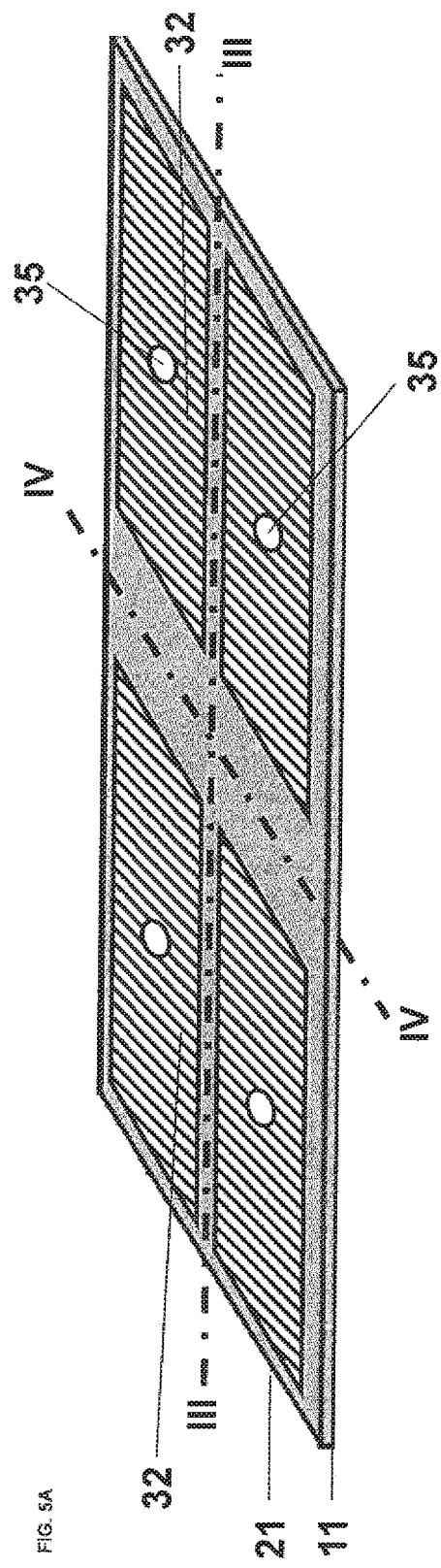
Figure 5B:
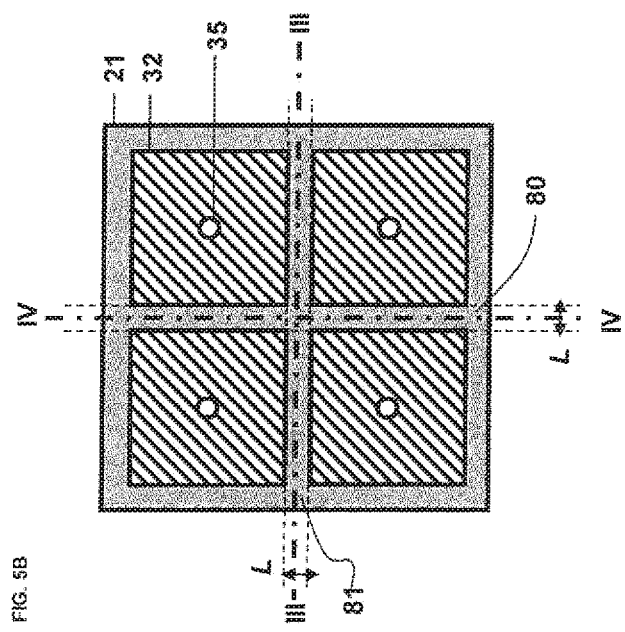
Figure 6:
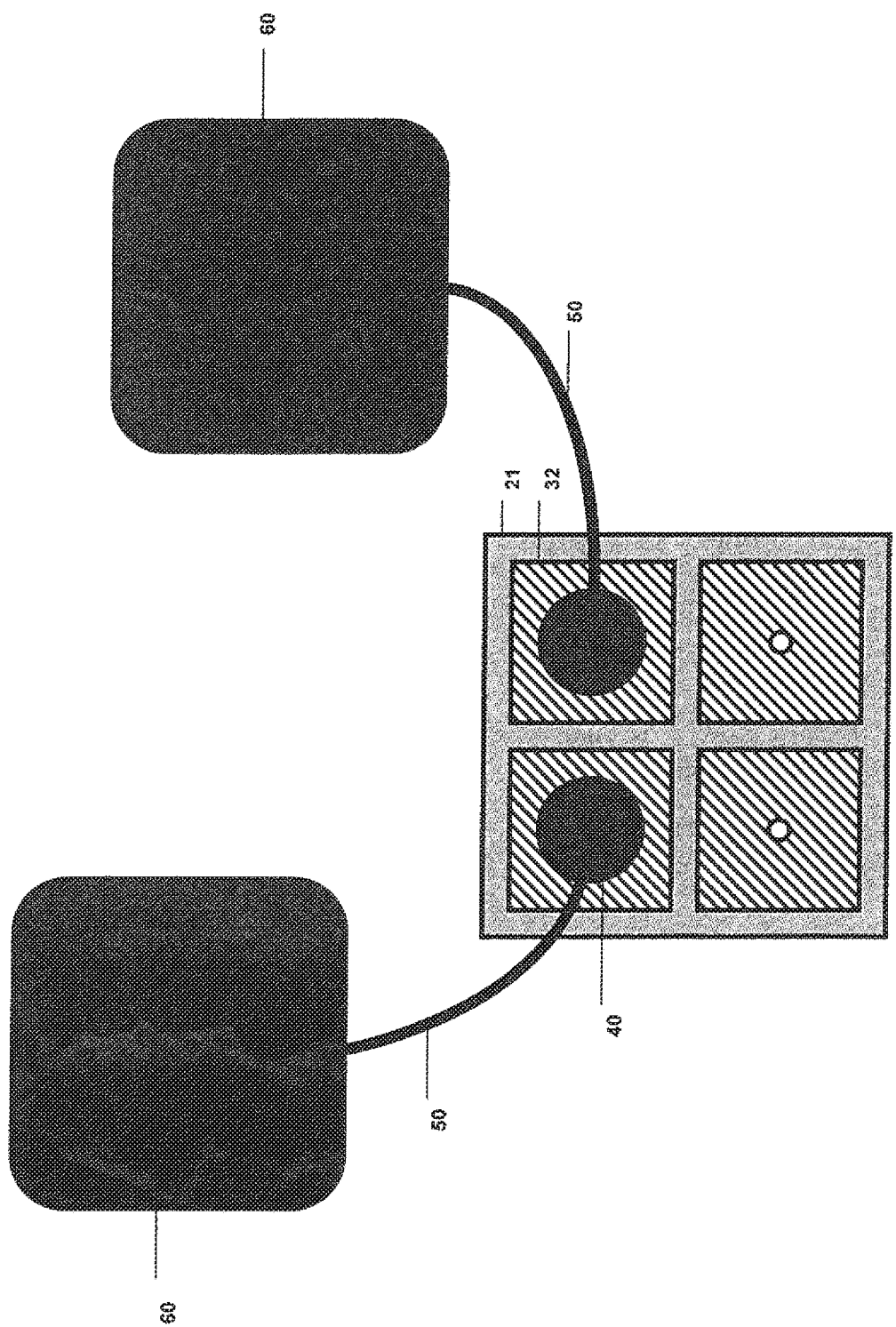
Figures 7A, 7B:
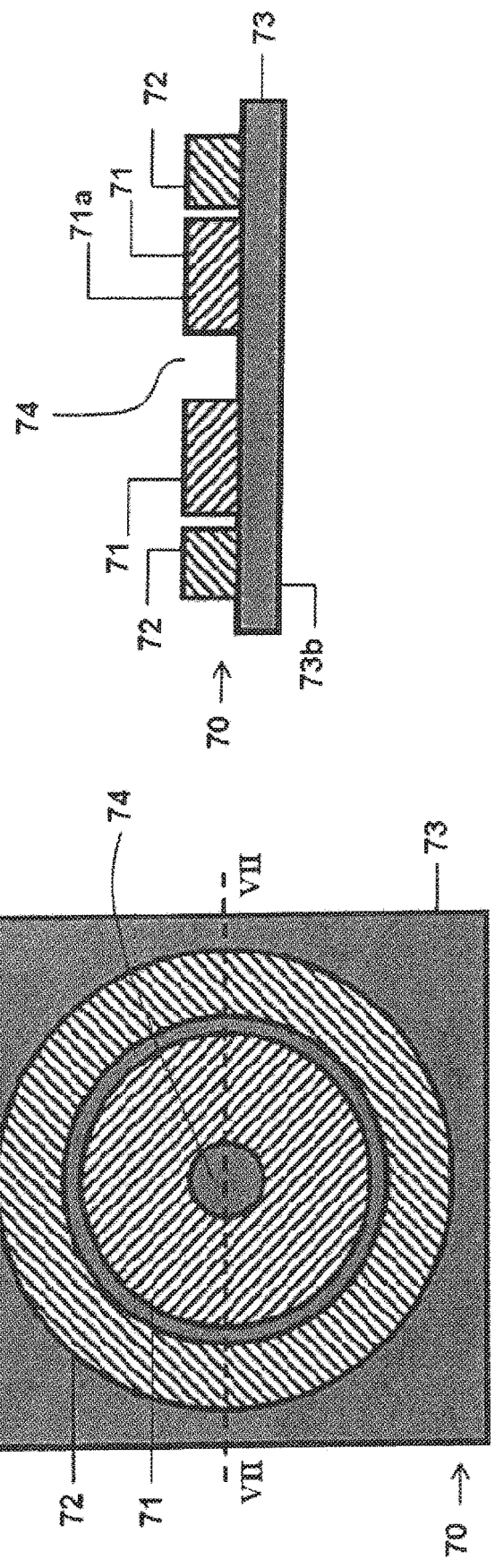

The invention will be better understood and other objects, advantages and features thereof will appear more clearly upon reading the description which follows and which is made with reference to the appended drawings, wherein:

FIG. 1 (1A-1D) comprises a top view (FIG. 1A of the lower layer of a device according to the invention, a top view (FIG. 1B) and a bottom view (FIG. 1C) of the intermediate layer of this device and a top view (FIG. 1D) of the upper layer of this device, FIG. 2 is a partial sectional view of the upper layer illustrated in FIG. 1D, assembled on the intermediate layer illustrated in FIGS. 1B and 1C, FIG. 3 (3A-3C) comprises a bottom view (FIG. 3A) and a sectional view (FIG. 3B) along the line II-II of FIG. 3A of a plug adapted to the device according to the invention illustrated in FIGS. 1 and 2, as well as a sectional view (FIG. 3C) illustrating the plug shown in FIGS. 3A and 3B connected to the device illustrated in FIGS. 1 and 2, FIG. 4 is an exploded and perspective diagram of the device illustrated in FIGS. 1 and 2, FIG. 5 (FIGS. 5A-5B) comprised a perspective view (FIG. 5A) and a top view (FIG. 5B) of the device according to the invention, after assembling, FIG. 6 is a top view of the device according to the invention illustrated in FIG. 5, connected to two cutaneous electrodes, and FIG. 7 (7A-7B) comprises a top view (FIG. 7A) and a sectional view (FIG. 7B) of an alternative of the electrical connection means illustrated in FIGS. 1D and 2.

The elements common to the different figures will be illustrated with the same references.

FIG. 1 schematically illustrates the device according to the invention, of the patch type.

The latter may be broken down into three layers:
a lower layer 1 which comprises a flexible sheet playing a role of lower encapsulation,
an intermediate layer 2 which comprises components mounted on a flexible circuit, and
an upper layer 3 which comprises elements fulfilling a dual function of electric connection and of mechanical protection of the components.

FIG. 1A is a top view illustrating the lower layer 1 which comprises a flexible sheet 11 playing a role of lower encapsulation.

The lower layer 1 is intended to be in contact with the skin of the user.

The flexible sheet 11 is for example a sheet in thermoplastic elastomer or in silicone, with a thickness comprised between 0.1 mm and 1 mm.

In the example illustrated in FIG. 1A, the layer 1 has a square shape. Other shapes are conceivable, notably a rectangular, circular or oval shape.

FIGS. 1B and 1C represent the intermediate layer 2, respectively in a top and bottom view. It comprises a flexible circuit 21, the upper face 21a of which is illustrated in FIG. 1B and the lower face 21b of which is illustrated in FIG. 1C.

In the illustrated example, the circuit 21 has a square shape. Other shapes are conceivable, notably a rectangular, circular or oval shape.

The flexible circuit 21 is for example supported by a sheet in polyimide with a thickness of 0.045 mm.

Metal tracks (not shown in the figures) are defined on the upper face 21a of the flexible circuit 21.

The metal tracks are for example copper tracks for which the thickness is of about 0.035 mm.

Assemblies 23 of components are mounted on the lower face 21b of the flexible circuit 21. In the illustrated example, each assembly 23 has a square shape and four assemblies are present on the lower face 21b.

Each assembly 23 may comprise electronic components, for example integrated circuits, resistors, inductors, capacitors or diodes, energy sources, for example battery cells, accumulators, batteries or super-capacitors or any other component.

Generally, all these components may be deteriorated if they undergo a stress.

The maximum thickness of the components within each assembly 23 is typically comprised between 0.1 mm and 5 cm. This thickness range is essentially set by the thicknesses of the energy sources which may be integrated in a pulse generator patch for electrical stimulation, from batteries with thin layers of the thickness of the order of a few hundred microns, up to batteries in packagings of the "button" or "pouch" type, the thickness of which is of the order of a few millimeters. Metal tracks (not shown in the figures) are defined on the lower face 21b of the flexible circuit 21 for interconnecting the components.

Vertical interconnections (not shown in the figures) give the possibility of connecting the components located on the lower face 21b with metal tracks located on the upper face 21a.

FIG. 1D is a top view illustrating the upper layer 3, which comprises elements 32.

Each element 32 plays a dual role of electrical connection and of mechanical protection, as this will now be explained in detail.

Reference is made in FIG. 2 which is a sectional view along the I-I line in FIG. 1D of an element 32 assembled on the flexible circuit 21 illustrated in FIGS. 1B and 1C.

The element 32 has a thickness noted as H and is delimited by an upper face 32a and a lower face 32b through which it is assembled on the upper face 21a of the flexible circuit 21.

More specifically, the lower face 32b of the element 32 is brazed to metal tracks defined on the upper face 21a of the flexible circuit 21 (not shown in the figures). Thus, the element 32 is electrically connected to the flexible circuit 21.

As this will be more specifically described with regard to FIG. 3, the element 32 may thus fulfill an electric connection function.

For this, the element 32 is designed so as to cooperate with the means for connecting a plug intended to be secured to an electric conductor.

In the example illustrated in FIGS. 1D and 2, the element 32 is pierced over the whole of its thickness with a hole 35. Therefore this is a through-hole.

This hole may notably be cylindrical. In this case, its diameter is advantageously comprised between 0.1 mm and 10 mm and preferably between 0.5 mm and 5 mm.

As an alternative, a plurality of through-holes may be provided in the element 32. This gives the possibility of facilitating the connection between the element 32 and the plug 40 described with reference to FIG. 3.

Moreover, the element 32 may not only fulfill an electric function but also a magnetic function. The benefit of this additional function will be described with reference to FIG. 3.

In this case, the element 32 is for example made in a ferromagnetic material, such as ferromagnetic steel.

FIGS. 3A and 3B illustrate a plug 40, respectively seen from below and a sectional view along the line II-II in FIG. 3A.

The plug 40 is secured to an electric cable 50, itself connected to a cutaneous electrode which is not illustrated in FIG. 3B.

The plug 40 is designed so as to cooperate with an element 32 in order to establish an electric connection between the device and a cutaneous electrode, as this will be described with reference to FIG. 6.

The plug 40 comprises a planar part 44, here with a cylindrical shape, forming the base of the plug and a protruding part 42 on this planar part forming a protrusion.

The part 44 comprises, in this example, a ring-shaped part 41 and a cylindrical part 43 at the center of the ring-shaped part 41. The three parts 41, 43 and 42 are centered around a same axis.

In this example, the part 41 fulfills a magnetic function.

This is for example a part in ferrite, aluminum-nickel-cobalt, samarium-cobalt or further in neodymium-iron-boron which are magnetized materials.

The part 43 fulfills an electric function. This is for example a metal part.

The part 42 is for example a polymeric part.

Other embodiments of the plug 40 may be contemplated.

In particular, the base 44 of the plug may be made in a single piece, for example one piece in a magnetized material and electrically conducting, notably in aluminum-nickel-cobalt, samarium-cobalt or neodynium-iron-boron. In this case, the protrusion 42 will for example be a metal part.

Moreover, in the example illustrated in FIG. 3B, the ring-shaped part 41 of the base 44 is slightly set back relatively to the cylindrical central part 43.

However, in another embodiment, both of these parts 41 and 43 may include the same thickness and be aligned.

Reference will now be made to FIG. 3C which illustrates the plug 40 once it is connected to an element 32.

The hole 35 receives the protrusion 42, which prevents accidental disconnection due to lateral forces, i.e. forces in the plane of the element 32.

The upper face 32a of the element 32 establishes an electrical contact with the central part 43. The element 32 and the part 41 exert on each other an attractive magnetic force.

In the exemplary embodiment of the plug 40 illustrated in FIG. 3, the electric contact between the upper face 32a and the part 43 is improved, as compared to an embodiment where the ring-shaped part 41 and the central part 43 have the same thickness.

Indeed, because the part 41 is slightly set back from the part 43, the pressure exerted by the part 43 on the upper layer 32a is increased. In other words, the electric resistance of the contact is reduced.

When the base 44 of the plug is made in a single piece, the electric contact between the plug and the element 32 is achieved between the upper face 32a of the element 32 and the whole surface of the base in contact with this upper face 32a.

The presence of parts fulfilling a magnetic function gives the possibility of facilitating the connection between the plug 44 and an element 32. Indeed, a small lateral displacement of the plug is sufficient so that the magnetic forces comes into action and assembled the plug 44 and the element 32, by causing insertion of the protrusion 42 of the plug in the hole 35 of the element 32.

However, it is not indispensable to provide parts fulfilling a magnetic function. Indeed, as this will appear in the following figures, the presence of several elements 32 on the device according to the invention already facilitates connection without any visual control, between the device and a plug for example connected to a cutaneous electrode.

The thickness H of each element 32 is selected so as to be sufficiently high so as to ensure lateral maintaining of the part 42 and therefore of the plug 40 in the element 32.

The thickness H of each element 32 is preferably comprised between 0.5 mm and 2 mm.

The surface of each element 32 and the surface of the ring-shaped part 41 are sufficiently large in order to ensure, by the magnetic attraction, the vertical maintaining of the ring-shaped part 41 and therefore of the plug 40.

The surface area of each element 32 is preferably comprised between 1 $cm^2$ and 10 $cm^2$.

FIG. 4 schematically illustrates an exploded and perspective view of the device illustrated in FIGS. 1 and 2.

It shows how the elements 32 fulfill their mechanical protection function.

Thus, FIG. 4 illustrates the three layers 1, 2 and 3 of the device according to the invention which are successively positioned above each other.

The upper layer 3 is thus found facing the upper face 21a of the intermediate layer 2 and the assemblies of components 23 of the intermediate layer 2 are facing the lower layer 1.

FIG. 4 shows that the assemblies 23 of components of the intermediate layer 2 as well as the elements 32 of the upper layer 3 are localized respectively in the intermediate layer 2 and in the upper layer 3, so that an element 32 of the upper layer 3 covers a set of components 23.

In practice, this may be obtained with elements 32 having a projection surface area on the intermediate layer 2 which is at least equal to the surface area of the set 23 of components with which it is associated and by positioning each element 32 in the upper layer 3 so that it is vertically aligned with a set 23 of components. In other words, an element 32 is aligned with a set of components according to the thickness of the stack of the three layers 1, 2 and 3.

In this case, each element 32 may actually cover a set 23 of components of the intermediate layer 2.

By this arrangement, the elements 32 ensure efficient mechanical protection of the components located in the sets 23, notably against impacts, piercing or stresses upon flexure of the patch. This is allowed by:

their thickness, which may for example be greater than 0.5 mm, their composition, the elements 32 may for example be made in steel which is a rigid and tough material.

The invention is not however limited to this embodiment. In practice, the connection means are not necessarily designed for protecting all the components present on the intermediate layer. Indeed, certain components less sensitive or less fragile may not be protected. It is therefore sufficient that the electrical connection means cover and protect at least one component. Thus, it is sufficient that the connection means be aligned with at least one component, along the thickness of the stack.

Moreover, in the examples illustrated earlier, the components are positioned on the lower face 21b of the intermediate layer 2.

However, the invention also relates to a device in which the components are positioned on the upper face 21a of the intermediate layer. In this case, the electric connection means are designed so as to have the shape of a lid.

FIGS. 5A and 5B schematically illustrate the device shown in FIG. 4 once it is assembled, respectively in a perspective view and a top view.

FIGS. 5A and 5B confirm that each set of components 23 present on the intermediate layer 2 is covered by an element 32.

Moreover, considering the thickness ranges indicated earlier for the different constitutive elements of the device, the maximum thickness of the obtained device is comprised between 1 mm and 8 mm.

Further, the total surface area of the patch is comprised between 5 cm$^2$ and 50 cm$^2$.

Thus, the device comprises a plurality of rigid areas, corresponding to the areas occupied by the elements 32, connected through flexible areas, corresponding to the remainder of the surface of the device.

In the example illustrated in FIG. 5, these flexible areas are two strips 80 and 81 of the flexible circuit 21 of the intermediate layer 2. These flexible areas 80 and 81 form here a cross between the four elements 32 of the device illustrated in FIG. 5.

The width L of the areas 80 and 81 is preferably comprised between 1 mm and 5 cm.

Of course, these flexible areas may have different shapes, according to the shape of the elements 32 and their distribution on the flexible circuit 21.

In the example illustrated in FIG. 5, the device according to the invention may be flexed along the axes III-III and IV-IV passing in the flexible areas 80 and 81 and illustrated in dotted lines in FIG. 5.

By means of the presence of these flexible areas, the device according to the invention may be adapted to different areas of the human body, because of its conformation capability.

Moreover, the elements 32 may fulfill a third function, in addition to their electrical connection function and to their mechanical protection function of the components. This function consists of limiting flexure of the device, i.e. limiting the radius of curvature at the flexible areas 80 and 81 to a determined value, which notably gives the possibility of protecting the metal tracks of the circuit 21 present at the flexible areas 80 and 81.

The elements 32 may fulfill this third function of limiting the radius of curvature in the following way: during flexure at one flexible area 80 or 81, two adjacent elements 32 come into contact with each other, thereby limiting the radius of curvature to a determined value. The minimum value of the radius of curvature depends on the width L of the flexible areas 80 and 81 and on the height H of the elements 32.

In order to obtain this effect of limitation of the radius of curvature, L and H should be selected so that $L<\pi H$ and, preferably, $L<2H$.

Thus, the device according to the invention comprises a plurality of connection means formed by the elements 32, each of them may cooperate with a plug 40 for ensuring the connection between the device and a cutaneous electrode for example.

FIG. 6 schematically illustrates a device according to the invention connected to two cutaneous electrodes 60.

Each cutaneous electrode 60 is connected to an electrical cable 50 secured to a plug 40 which cooperates with an element 32 of the device for establishing an electric connection between the device and the cutaneous electrode 60.

Thus, in the example illustrated in FIG. 6, the device is connected to two cutaneous electrodes 60, typically a cathode and an anode and comprises four electrical connection means 32.

The fact of having a number of connection means 32 (four in this example) greater than the number of plugs 40 to be connected (two in this example) is advantageous, since this provides the user with great freedom in the positioning of the cutaneous electrodes on the body, for a given position of the device.

This also facilitates the making of the connection since several connection possibilities are provided to each plug.

In an alternative of the device described in FIGS. 1 to 6, rigid elements may be added in the rear face of the device, for example on the face of the flexible sheet 11 opposite to the intermediate layer 2.

Each of these additional rigid elements (not shown in the figures) is vertically aligned with a set 23 of components. Thus, these additional rigid elements contribute to mechanical protection of the components located in the sets 23.

Further, these additional rigid elements may ensure a function for limiting the radius of curvature, in the same way as the elements 32.

In an alternative of the device described in FIGS. 1 to 6, the elements 32 may be replaced with other types of elements, also fulfilling a dual role of electric connection and of mechanical protection. For example, each element 32 may be replaced with an element 70 described in FIG. 7.

The element 70 comprises a central ring-shaped part 71 fulfilling an electric function. The part 71 is for example a metal part.

The element 70 also comprises a ring-shaped part 72 surrounding the ring-shaped part 71 and fulfilling a magnetic function. The part 72 is formed in a magnetized material, for example ferrite, aluminium-nickel-cobalt, samarium-cobalt or neodymium-iron-boron.

Both ring-shaped parts 71 and 72 are centered around a same axis, and define in their center a hole 74.

The element 70 finally comprises a planar part 73, formed in a rigid material, for example a polymeric material like epoxy resin. The part 73 fulfills a mechanical function, while maintaining both parts 71 and 72 in a same plane.

The lower face 73b of the part 73 is intended to be adhesively bonded on the upper face 21a of the flexible circuit 21. Vertical interconnections made in the part 73 and in the flexible circuit 21 (not shown in the figures) give the possibility of electrically connecting the part 71 to the metal tracks of the circuit 21.

Each element 70 fulfills a role of electric connection. Thus, a plug 40 may cooperate with an element 70 in order to establish an electrical connection between the device and a cutaneous electrode.

The hole 74 of the element 70 then receives the protrusion 42 of the plug 40, which prevents accidental disconnection due to lateral forces, i.e. forces in the plane of the part 73.

The upper face 71a of the part 71 establishes an electric contact with the central part 43 of the plug 40.

The part 72 of the element 70 and the part 41 of the plug 40 exert on each other an attractive magnetic force.

As mentioned earlier, the part 73 of the element 70 maintains both parts 71 and 72 in a same plane, which ensures:

good electric contact between the part 71 and the part 43 when the part 72 and the part 41 exert on each other an attractive magnetic force;

a maximum magnetic attraction between the part 72 and the part 41 when the part 71 and the part 43 are in electrical contact.

The main advantage of an element 70 as compared to an element 32 is the following. In the case when the user seeks to connect a plug 40 in an element 70, the magnetic attraction is exerted between two magnetized ring-shaped parts (the part 72 of the element 70 and the part 41 of the plug 40), which gives the possibility of very efficiently guiding the protrusion 42 of the plug 40 in the hole 74 of the element 70, since two ring-shaped magnets tend to be aligned, i.e. centered around a same axis.

As a comparison, in the case when the user seeks to connect a plug 40 in an element 32, the magnetic attraction is exerted between a magnetized ring-shaped part (the part 41 of the plug 40) and a part formed in a ferromagnetic metal (the part 32), which may lead to situations where the plug and the element 32 are not properly aligned and therefore when it is more difficult to have the protrusion 42 penetrate into the hole 35.

This drawback may be overcome by providing a plurality of through-holes in the elements 32.

Like the elements 32, each element 70 also fulfills a role for mechanical protection of the components located in the assemblies 23, notably against impacts, piercing or stresses upon flexure of the patch.

This is allowed by:
the thickness of the elements 70, which may be greater than 0.5 mm,
the composition of the elements 70, which are made by assembling rigid and tough materials, for example a metal (part 71) and an epoxy resin (part 73).

Finally, as this was described for the elements 32 with reference to FIG. 5, the elements 70 may also fulfill a function of limiting the flexure at the flexible areas located between two adjacent elements.

The reference signs inserted after the technical characteristics appearing in the claims only have the purpose of facilitating the understanding of the latter and cannot limit the scope thereof.

The invention claimed is:

1. An assembly, comprising:
a cutaneous electrode,
an electric cable secured to a plug, and
a substantially planar device attachable to the skin of a user, comprising:
a face configured to be in contact with the skin of a user;
first and second electronic components; and
first and second electrical connection elements,
the first electrical connection element forming a first rigid area covering the first electronic component, the second electrical connection element forming a second rigid area covering the second electronic component, each of the first and second electrical connection elements having a planar upper surface and a planar lower surface, wherein the first electronic component is positioned between the first electrical connection element and the face, and the second electronic component is positioned between the second electrical connection element and the face, the first and second electrical connection elements providing mechanical protection of the first and second electronic components, respectively,
the cutaneous electrode being connected to the electric cable secured to the plug which cooperates with any one of said first and second electrical connection elements.

2. The assembly of claim 1, wherein the first and second rigid areas are electrically and mechanically connected to a flexible area extending therebetween, the first electronic component being mounted to the first rigid area.

3. The assembly of claim 2, wherein the second electronic component is mounted to the second rigid area, the flexible area having a width L, the first and second electrical connection elements having a height H, wherein $L<\pi H$.

4. The assembly of claim 3, wherein $L<2H$.

5. The assembly of claim 2, wherein the second electronic component is mounted to the second rigid area.

6. The assembly of claim 1, wherein the each of the first and second electrical connection elements has, in the plane of the device, a surface area greater than that occupied by the corresponding electronic component, and is aligned with the corresponding electronic to cover the corresponding electronic component.

7. The assembly of claim 1, wherein the upper surface of the first electrical connection element includes at least one opening configured to cooperate with the plug.

8. The assembly of claim 1, wherein the device comprises first and second layers forming a stack, the first layer comprising the first and second electrical connection elements, and the second layer comprising the first and second electronic components and a flexible circuit element, wherein the first and second electronic components are mounted on the flexible circuit element.

9. The assembly of claim 8, further comprising a third flexible layer in contact with the second layer, the third layer cooperating with the first layer to encapsulate the second layer.

10. The assembly of claim 8, wherein the first rigid area covers a first area of the flexible circuit element occupied by the first electronic component.

11. The assembly of claim 10, wherein the second rigid area covers a second area of the flexible circuit element occupied by the second electronic component.

12. The assembly of claim 1, wherein the first electrical connection element comprises a ferromagnetic metal.

13. The assembly of claim 1, further comprising a first complementary rigid element positioned proximate to the first electronic component, the first electronic component being disposed between the first rigid area and the first complementary rigid element.

14. The assembly of claim 13, further comprising a second complementary rigid element positioned proximate to the second electrical connection element, the second electronic component being disposed between the second rigid area and the second complementary rigid element.

15. The assembly of claim 1, wherein each of the first and the second electronic components is at least one of an integrated circuit, a resistor, an inductor, a capacitor, a diode, a battery cell, an accumulator, a battery, and a supercapacitor.

16. The assembly of claim 1, wherein the first and the second electrical connection elements are configured to cooperate with the plug to provide electrical connection between the device and the cutaneous electrode.

* * * * *